(12) United States Patent
Kim et al.

(10) Patent No.: US 7,708,908 B2
(45) Date of Patent: May 4, 2010

(54) CARBOXYLIC ACID-MODIFIED EDOT FOR BIOCONJUGATION

(75) Inventors: Jinsang Kim, Ann Arbor, MI (US); Jae Cheol Cho, Ann Arbor, MI (US); Laura K. Povlich, Ann Arbor, MI (US); David C. Martin, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 239 days.

(21) Appl. No.: 12/038,138

(22) Filed: Feb. 27, 2008

(65) Prior Publication Data

US 2008/0224099 A1 Sep. 18, 2008

Related U.S. Application Data

(60) Provisional application No. 60/904,118, filed on Feb. 28, 2007.

(51) Int. Cl.
*H01B 1/12* (2006.01)
*C08G 75/00* (2006.01)
*C07D 333/10* (2006.01)
*G01N 31/00* (2006.01)

(52) U.S. Cl. .......... 252/500; 528/377; 549/29; 422/79

(58) Field of Classification Search .......... 252/500; 528/377; 549/29, 60; 422/79, 82.02; 600/372; 607/115
See application file for complete search history.

(56) References Cited

U.S. PATENT DOCUMENTS 6,403,741 B1 * 6/2002 Heuer et al. ........... 526/256

(Continued)

FOREIGN PATENT DOCUMENTS

WO  WO 2006/018643  * 2/2006

(Continued)

OTHER PUBLICATIONS

Povlich et al "Carboxylic Acid-Modified EDOT for Bio-Functionalization of Neutral Probe Electrodes", Polymer Preprints (ACS) (2007), 48(1), 7-8; Spring Meeting Mar. 2007.*

(Continued)

*Primary Examiner*—Mark Kopec
(74) *Attorney, Agent, or Firm*—Harness, Dickey & Pierce, P.L.C.

(57) ABSTRACT

An electroconductive carboxylic acid functionalized monomer corresponding to Formula (I), wherein A represents a hydrogen or a carboxyl group. Polymerized monomers of Formula (I) conjugated with a biomolecule result in conjugated PEDOT polymers of Formula (III) wherein A is a hydrogen or a carboxylic acid group and B is a biomolecule selected from the group consisting of a peptide, a protein, a lipid, a carbohydrate and a polynucleotide. The biomolecule conjugated polymers can be disposed onto an electrically conductive substrate wherein the substrate has a first layer of PEDOT polymerized on a surface of the substrate and a second layer of biomolecule conjugated PEDOT polymer of Formula (III) polymerized on the first layer of PEDOT. The first and second layers form a charge transport material in electrical communication with the conductive substrate. The electrically conductive substrate further comprises a dopant.

20 Claims, 9 Drawing Sheets

U.S. PATENT DOCUMENTS 6,730,212 B1 * 5/2004 Yamagishi et al. ....... 205/777.5
6,890,715 B1 * 5/2005 Lewis et al. .................... 435/6

FOREIGN PATENT DOCUMENTS

| WO | WO 2008/130326 | * | 10/2008 |
| WO | WO 2009/054814 | * | 4/2009 |

OTHER PUBLICATIONS

Mouffouk et al "Oligonucleotide-functionalized poly(3,4-ethylenedioxythiophene)-coated microelectrodes . . . ", Electrochem Comm 8 (2006) 317-322.*

Malhotra et al "Prospects of conducting polymers in biosensors", Abalytica Chimica Acta 578 (2006) 59-74.*

Lee et al "Carboxylic Acid-Functionalized Conductive Polypyrrole as a Bioactive Platform for Cell Adhesion", Biomacromolecues 2006, 7, 1692-1695.*

* cited by examiner

Mass Spectroscopic data for Final compound
Mass (exact) = 186.0
Mass (observed) = 186.0

CARBOXYLIC ACID-MODIFIED EDOT FOR BIOCONJUGATION

CROSS-REFERENCE TO RELATED APPLICATIONS

This application claims the benefit of U.S. Provisional Application No. 60/904,118 filed on Feb. 28, 2007. The disclosure of the above application is incorporated herein by reference.

STATEMENT OF GOVERNMENT RIGHTS

This invention was made with Government support under Contract No. DMR0158079 awarded by the National Science Foundation and Contract No. W911NF-06-1-0218 awarded by the Army Research Office. The U.S. Government has certain rights in this invention.

FIELD

The present disclosure relates to compositions comprising carboxylic acid-modified 3,4-ethylenedioxythiophene (EDOT) and methods of functionalizing and conjugating electrically conductive monomers and polymers with bioactive molecules to promote cellular interactions with the electrically conductive polymers.

BACKGROUND

The statements in this section merely provide background information related to the present disclosure and may not constitute prior art.

Coatings composing the charge-transporting polymer poly (3,4-ethylenedioxythiophene) (PEDOT) have been developed for biomedical electronic devices such as neural probes. See Cui et al., *Sensors and Actuators* (2003) 89:92-102 which is hereby incorporated in its entirety. Although the morphology and conductivity of PEDOT make it useful as a bioelectrode coating, a more bioactive film would be preferable.

When a neural probe is contacted with a conductive polymer for example polythiophene or PEDOT or PEDOT derivative, inherent problems are easily found during in vivo use. When a probe is inserted into living tissue, for example, the brain, there is a reactive inflammatory response, because the electrode surface lacks the proper functionality to interact with the cells at the site of implantation.

Therefore, in order to maintain the recording and stimulating capabilities of neural devices, it is necessary to develop materials that reduce the brain immune response, increase the likelihood of establishing biocompatible connections between the electrode and the brain cells and materials that favor the attraction of neurons to the electrode over less favorable cell types like glial cells.

At present, electrodes comprising of PEDOT coatings have been designed to increase the total surface area of the electrode and enable the electrode to interact with fine cellular processes in order to make them more biocompatible. However, the present PEDOT coated electrodes are not sufficiently biologically compatible with the cells and tissues into which they are implanted.

PCT Application WO 2006/018643 describes sensors that comprise a conjugate having a ligand attached to EDOT or derivative and polymer thereof by means of a spacing element. This application illustrates an example of nucleic acid coupling to EDOT via the synthesis of an acid functionalized EDOT. The synthesis process yields a 2,3-dihydro-thieno[3,4-b][1,4]dioxin-2-ylmethyl ester which can be coupled to a nucleic acid using (dimethylaminopropyl)-3-ethyl-carbodiimide hydrochloride as a coupling agent. However, several drawbacks of using the ester or ether forms of carboxylic acid functionalized EDOT appear when used in a biological system. These drawbacks include enzymatic cleavage of the conjugated polymer at the ester bond by esterases, for example acetylcholinesterase, thus limiting the sensor or film's ability to interface with biological tissue. Also, since the ester form of carboxylic acid functionalized EDOT has a longer alky chain, it is less water-soluble than the carboxylic acid described in this application.

Further areas of applicability will become apparent from the description provided herein. It should be understood that the description and specific examples are intended for purposes of illustration only and are not intended to limit the scope of the present disclosure.

SUMMARY

The invention comprises a conductive polymer film or coating comprising at least one layer comprising a polymer polymerized with a monomer of Formula (I):

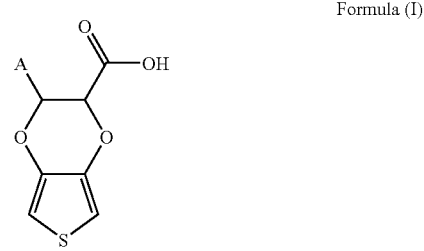

Formula (I)

In a further aspect, the present disclosure provides for the synthesis and use of electroconductive carboxylic acid functionalized monomers conjugated to one or more biomolecules, wherein the carboxylic acid group of the monomer can be coupled to an amino group on the biomolecule with a carbodiimide containing compound to form an amide bond with the biomolecule.

In still a further aspect, the present disclosure provides a biologically enhanced electroconductive polymer and methods for using the polymer. The polymer comprises a biomolecule conjugated PEDOT polymer of Formula (III):

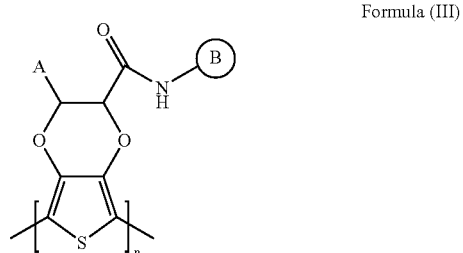

Formula (III)

The polymer used to make the structure shown in Formula (III) contains a first or a second carboxylic acid functional group. The A shown in Formula (III) can be a hydrogen or a carboxylic acid group and B can be a biomolecule selected from the group consisting of a peptide, a protein, a lipid, a carbohydrate and a polynucleotide.

In still a further aspect, the present disclosure provides an electrically conductive substrate. The substrate can have a first layer of PEDOT polymerized on a surface of the conductive substrate and a second layer of biomolecule conjugated PEDOT polymer of Formula (III) polymerized on the first layer of PEDOT. After the first and second layers have been electropolymerized on the substrate, the electropolymerized first and second layers form a charge transport material in electrical communication with the conductive substrate. The electrically conductive substrate further comprises a counter ion or dopant in order to perform the electropolymerization of the layers and for transferring charge from the conductive substrate to the material comprising the first and second layers.

DRAWINGS

The drawings described herein are for illustration purposes only and are not intended to limit the scope of the present disclosure in any way.

Figure 8:
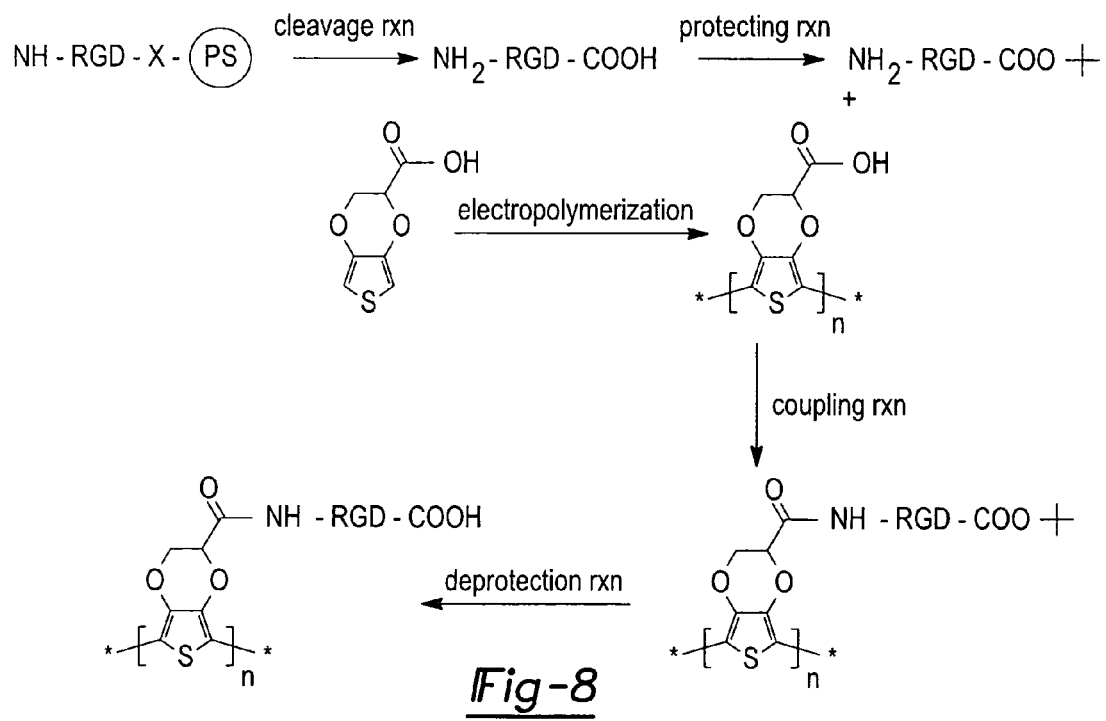

FIG. 8 depicts a general scheme for making a bioconjugated PEDOT film. First a solution of EDOT is electropolymerized as a first layer on the surface of a conductive substrate. Then a second layer of carboxylic acid EDOT is electropolymerized on the surface of the first layer. The second layer of carboxylic acid PEDOT is then conjugated to a peptide (GRGDS) by coupling the amino containing groups of the peptide to the COOH groups of the PEDOT using carbodiimide coupling chemistry. The resultant film is conjugated with a biomolecule providing a biologically enhanced film for interaction with electrically active cells like neurons.

Figure 9:
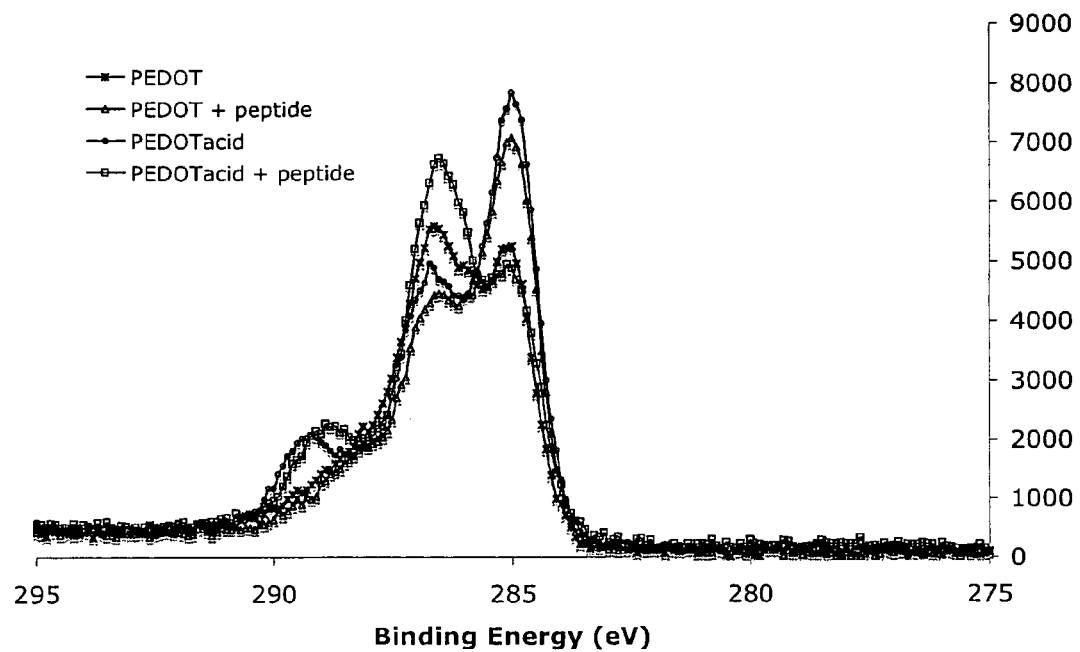

FIG. 9 illustrates a graph showing the C 1s XPS spectra for the PEDOT, carboxylic acid-PEDOT homopolymer film, PEDOT treated with GRGDS peptide and the carboxylic acid PEDOT-GRGDS peptide copolymer film. The conducting polymer films incorporated lithium perchlorate dopant. Samples treated with GRGDS peptide were washed extensively to remove unbound peptide.

Figure 10:
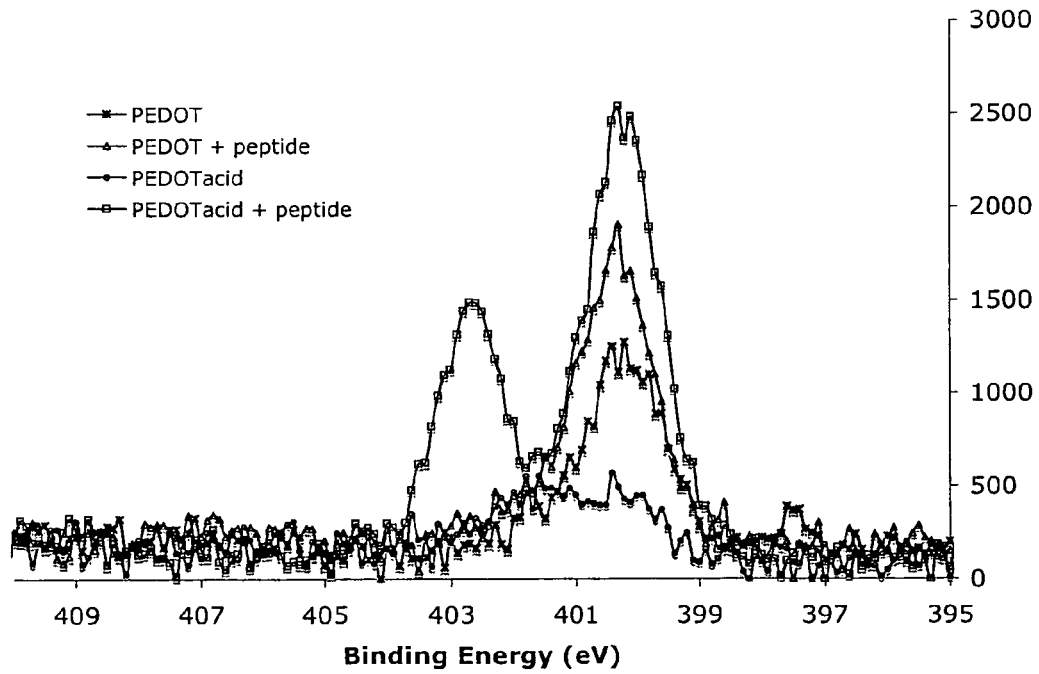

FIG. 10 illustrates a graph showing the N 1s XPS spectra for the PEDOT, carboxylic acid-PEDOT homopolymer film, PEDOT treated with GRGDS peptide and the carboxylic acid PEDOT-GRGDS peptide copolymer film. The conducting polymer films incorporated lithium perchlorate dopant. Samples treated with GRGDS peptide were washed extensively to remove unbound peptide.

Figure 11:
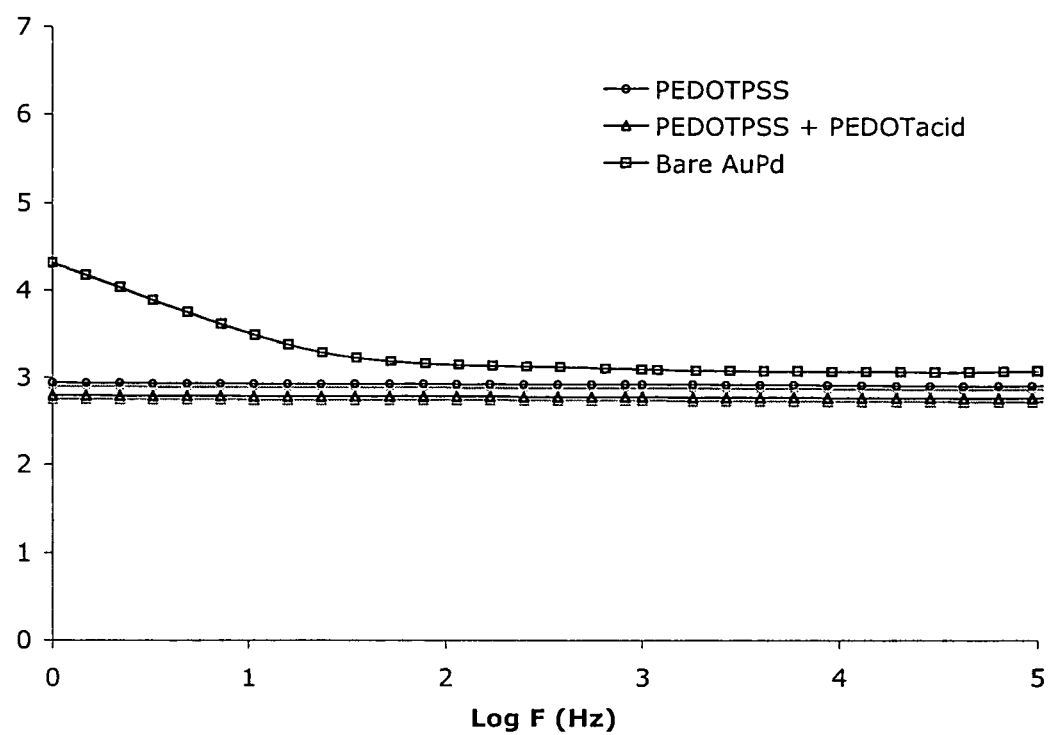

FIG. 11 depicts an EIS spectra for a PEDOT homopolymer film, a carboxylic acid PEDOT homopolymer film on top of a layer of PEDOT with PSS dopant and a bare Au/Pd electrode are compared.

Figure 12:
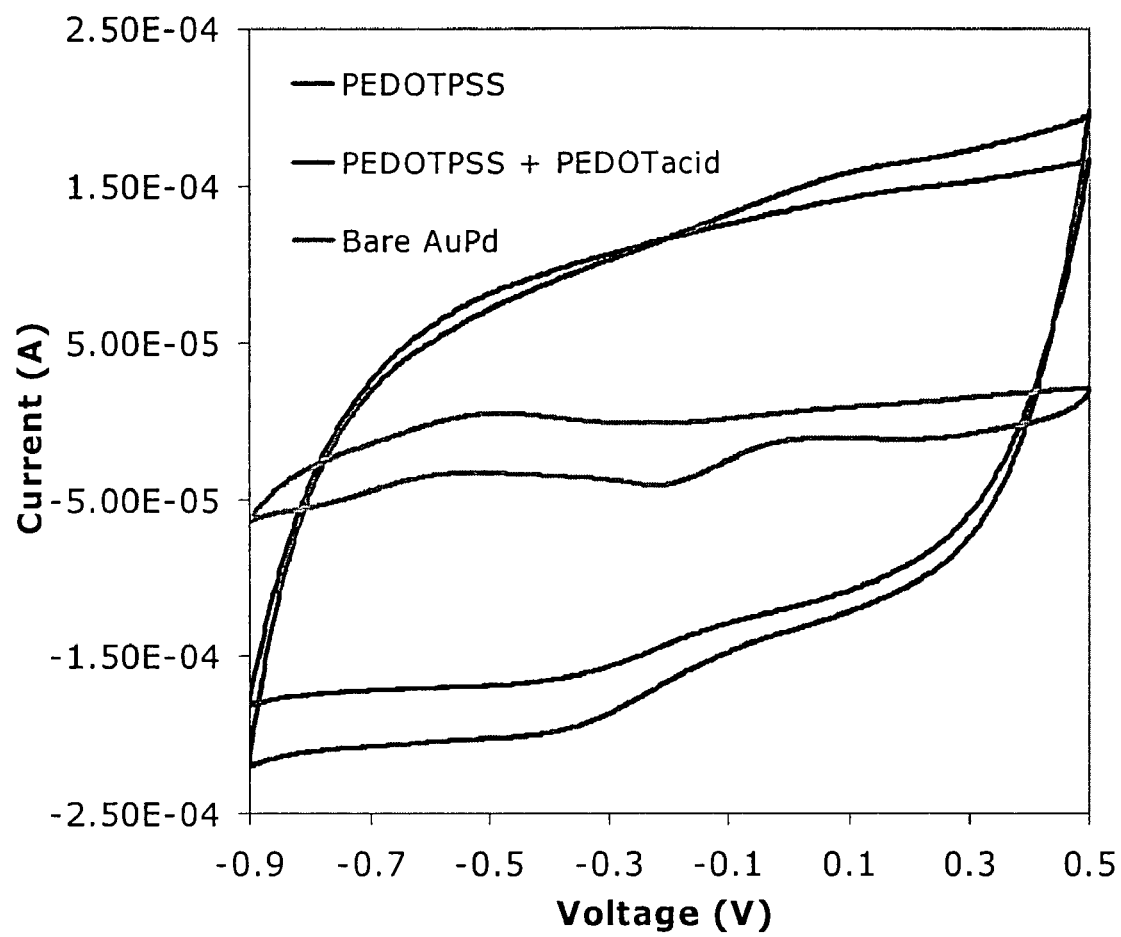

FIG. 12 depicts cyclic voltammetry (CV) curves of carboxylic acid PEDOT on top of a layer of PEDOT and PEDOT coatings, all with PSS dopant, for an average of 5 cycles. The CV curves shown in FIG. 12, demonstrate that different behavior between the carboxylic acid PEDOT and PEDOT coatings.

Figures 13A, 13B:
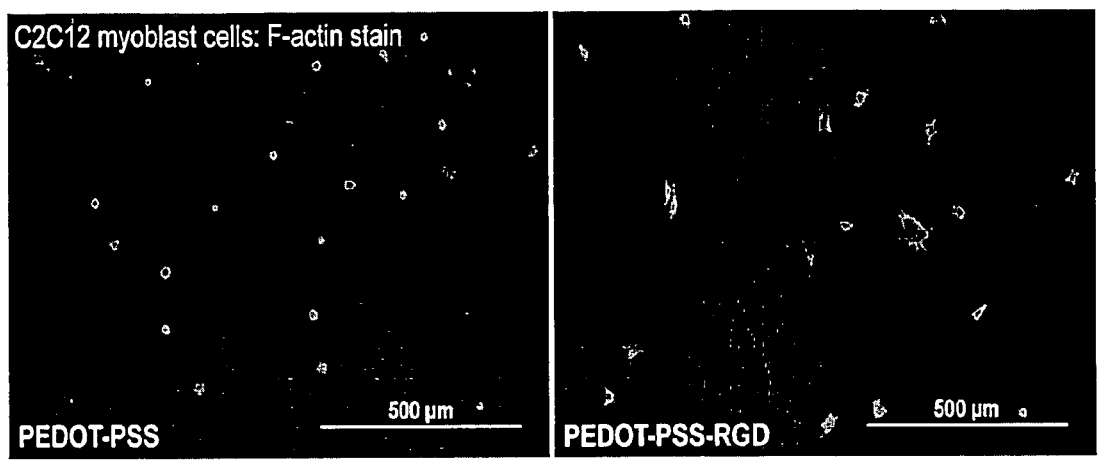

FIG. 13A is a photomicrograph of F-actin staining of C2C12 mouse skeletal muscle cells on PEDOT-PSS. Cells were seeded for 4 hours before fixing with formaldehyde and then staining with phalloidin.

FIG. 13B is a photomicrograph of F-actin staining of C2C12 cells on PEDOT-PSS-RGD. Cells were seeded for 4 hours before fixing with formaldehyde and then staining with phalloidin.

DETAILED DESCRIPTION

The following description is merely exemplary in nature and is not intended to limit the present disclosure, application, or uses.

The present disclosure provides a carboxylic and dicarboxylic acid functionalized electroconductive monomer 3,4-ethylenedioxythiophene (EDOT) according to Formula I, wherein A can be a hydrogen or a carboxylic acid. The disclosure also provides for polymerized carboxylic acid-PEDOT films and coatings on various solid and flexible substrates wherein the polymerized carboxylic acid EDOT monomer or carboxylic acid PEDOT can be further conjugated to biomolecules via its functionalized carboxylic acid group using standard coupling chemistries. The biomolecules can include, for example, peptides, for example, RGD, GRGDS, IKVAV, CDPGYIGSR, YIGSR, KDEL and combinations thereof (for example RGD-YIGSR), proteins, nucleic acids for example, deoxyribonucleic acids (DNA) consisting of small polynucleotide or oligonucleotide lengths of 7-50 nucleotides, nucleic acids of 50-10 kbp, ribonucleic acid (RNA), snRNA, siRNA, miRNA, nucleic acid mimetics, PNAs and combinations thereof), lipids, carbohydrates, including saccharides and polysaccharides and other organic compounds having a compatible coupling functional group to couple COOH groups. The conjugated carboxylic acid PEDOT polymer when disposed as a film or coating on a substrate or electrode, enhances the film or coating's biocompatibility with cells, cellular components, tissues and other biological samples.

In some embodiments of the present disclosure, conductive polymers can impart desirable features. For example, they are electrically stable over time following implantation in tissue; are relatively non-biodegradable, yet highly biocompatible; and elicit lower levels of immunoreactivity than commonly used conducting materials (such as silicon, platinum, iridium, indium tin oxide, and tungsten). As used herein, conductive polymers are conjugated polymers that are capable of conducting electrons. The term "conductive polymer(s)" is used interchangeably with "conducting polymer(s)." Conductive polymers are formed from their monomeric form (as used herein "conducting monomers") via electrochemical polymerization, oxidative polymerization, actinic radiation polymerization and other methods commonly used in the art. Conducting polymer polymerized around an electrically conductive substrate can also be referred to as a conducting polymer network due to its three dimensional, fuzzy, soft fibrils that extend out from the electrically conductive substrate. In some embodiments, the conducting polymer network contains embedded biological components including cells, cellular constituents, bioactive molecules or substances and combinations thereof.

Synthesis of Carboxylic Acid EDOT

Scheme 1. Synthesis of 2,3-dihydrothieno[3,4-b][1,4]dioxin-2-carboxylic acid (8), herein referred to as carboxylic acid EDOT monomer.

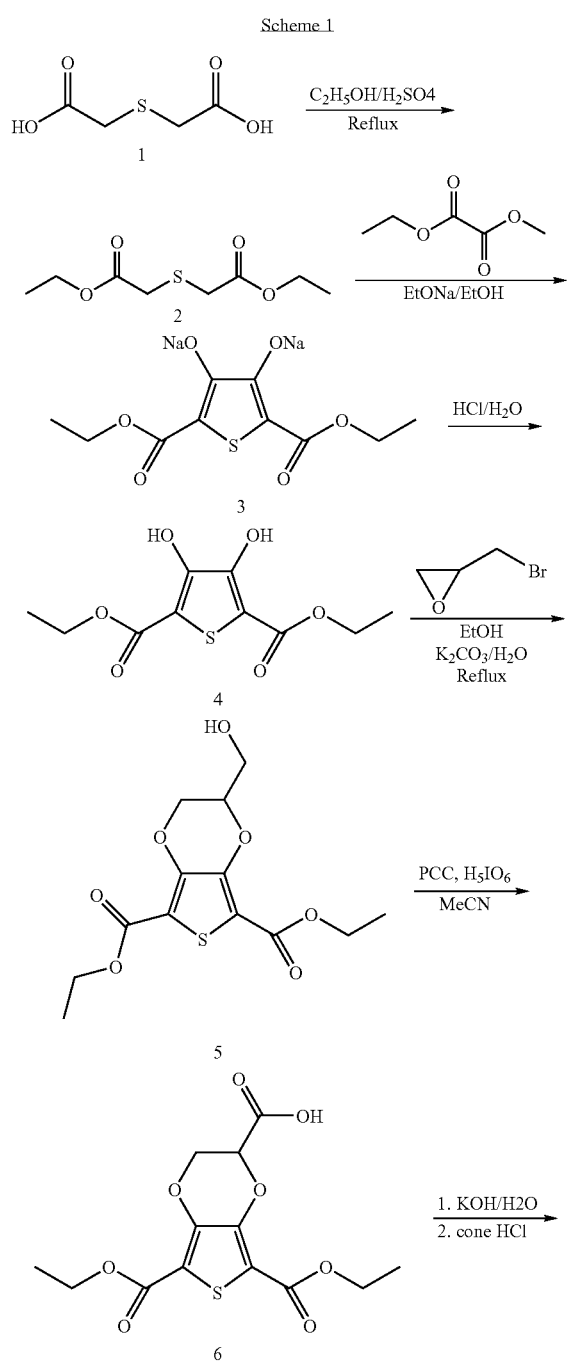

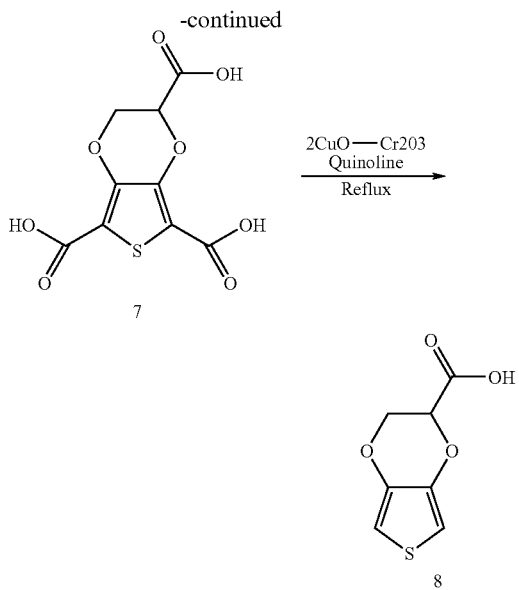

Carboxylic acid EDOT monomer can be synthesized, as shown in Scheme 1. Products formed and reacted are designated by Arabic numerals. First thiodiglycolic acid (1, 25 g, 0.17 mol) is refluxed with 10 ml sulfuric acid in 100 ml ethanol for 12 hours. The solution is cooled, diluted with 150 ml of water, and the product is extracted into diethyl ether three times. The organic layer is then washed three times with $Na_2CO_3/H_2O$, dried with $MgSO_4$ and the solvent is removed to produce 27.06 g of diethyl thiodiglycolate (2, 79% yield). Diethyl thioglycolate (27.06 g, 0.13 mol) is then added dropwise with diethyl oxalate (50 g, 0.34 mol) to 250 ml of sodium ethoxide (0.58 mol) at 0° C. After complete addition the solution is refluxed for 1 hour to form diethyl 3,4-dihydroxythiophene-2,5-dicarboxylate disodium salt (3). After filtration, (3) is acidified using hydrochloric acid, and the precipitate is filtered and washed with water. The product, diethyl 3,4-dihydroxythiophene-2,5-dicarboxylate (4), is dried and recrystallized in methanol to produce a yield of 27.02 g (80%). Next, (4) (8.75 g, 0.034 mol) is added to 200 ml of boiling ethanol. Epibromohydrin (3.75 ml, 0.045 mol) and $K_2CO_3$ (0.94 g in 50 ml water) are added to the reaction. After 30 minutes, more epibromohydrin (6.5 ml, 0.079 mol) and $K_2CO_3$ (0.5 g) are added and the solution is refluxed for 60 hours. The product is diluted with 150 ml of acidified water (5% HCl) and extracted two times with chloroform. The organic layer is then washed with 5% aqueous KCl, dried with $MgSO_4$, and the solvent is evaporated. The product, diethyl 2-(hydroxymethyl)-2,3-dihydrothieno[3,4-b][1,4]dioxin-5,7-dicarboxylate (5) is purified by precipitation in diethyl ether. The by-product, diethyl 2-hydroxy-2,3-dihydrothieno[3,4-b][1,4]dioxin-5,7-dicarboxylate, is also present with (5) but this compound cannot react in the next step so it is not separated from (5). Oxidation of the hydroxyl group on (5) is achieved by adding a catalytic amount of pyridinium chlorochromate (0.18 g, 0.8 mmol) and (5) (8.54 g, mixture with by-product) to a cooled solution (0° C.) of periodic acid (15 g, 0.066 mol) in 240 ml of acetonitrile. The solution is stirred for 3 hours as it warms to room temperature. After the reaction, the solution is diluted with 300 ml of ethyl acetate, washed with a 1:1 solution of brine:water, and the product is extracted into a solution of sodium bicarbonate and water. The aqueous later is then acidified with HCl and the product is extracted into ethyl acetate. The organic layer is then dried with MgSO$_4$ and the solvent is removed. The product, diethyl 2-(carboxylic acid)-2'-dihydrothieno[3,4-b]dioxin-5,7 dicarboxylate (6), is recrystallized in xylenes to produce a 26% yield from compound (4) to compound (6). Compound (6) (2.8 g) is then reacted with KOH (3 g, 0.05 mol) in 75 ml of water and 30 ml of ethanol for 1 hour at 60° C. After the reaction the solvent is removed and the product is washed with ethanol. The product is then filtered, dissolved in 150 ml of water and acidified with HCl. The product, diethyl 2-(carboxylic acid)-2,3-dihydrothieno[3,4-b][1,4]dioxin-5,7-dicarboxylic acid (7), is recovered as a white precipitate after stirring in acidified water for 3 hours in ~100% yield (2.36 g, 8.6 mmol). Compound (7) (2.36 g) is decarboxylated by refluxing with copper chromite catalyst (0.24 g, 0.76 mmol) in 14 ml of freshly distilled quinoline at 160-170° C. for 2 hours. The solution is diluted with ethyl acetate and filtered to remove catalyst. The product is then washed with 5% HCl three times, NaCl/water twice and extracted into 2% KOH. The aqueous layer is then acidified with HCl and the product is extracted into ethyl acetate, dried with MgSO$_4$ and the solvent is removed to produce 1.17 g (75% yield) of the final product, 2,3-dihydrothieno[3,4-b][1,4]dioxin-2-carboxylic acid i.e. carboxylic acid EDOT (8). This reaction scheme results in a total yield from compound 1 to compound 8 of 12%.

Products (2), (4), (6), (7) and (8) from Scheme 1 are verified using NMR, as shown in FIGS. 1-5, along with the coupling constants, J, shown below. Electron impact mass spectrometry was performed on product (8), and a peak at 186.0 also confirmed the synthesis of carboxylic acid EDOT.

compound (4)

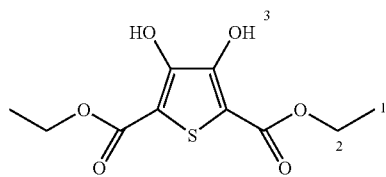

(400 MHz, d$^6$-DMSO) δ ppm (J Hz): 1.214 (t, 6H, J$_{1,2}$ 7.2 Hz, H$^1$), 4.205 (q, 4H, J$_{2,1}$ 7.2 Hz, H$^2$), 10.305 (br s, 2H, H$^3$)

compound (6)

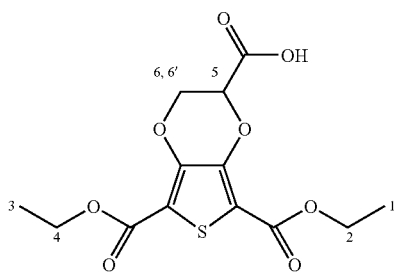

(400 MHz, d$^6$-DMSO) δ ppm (J Hz): 1.203 (t, 3H, J$_{1,2}$ 7.2 Hz, H$^1$), 1.215 (t, 3H, J$_{3,4}$ 7.2 Hz, H$^3$), 4.158-4.278 (m, 4H, H$^2$, H$^4$), 5.281 (t, 1H, J$_{5,6}$ 2.8 Hz, H$^5$), 4.599 (dd, 1H, J$_{6,5}$ 2.8 Hz, J$_{6,6'}$ 2.0 Hz, H$^6$), 4.382 (dd, 1H, J$_{6',5}$ 2.8 Hz, J$_{6',6}$ 12.0 Hz, H$^{6'}$)

compound (7)

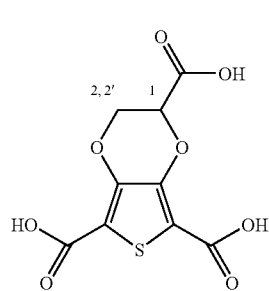

(400 MHz, d$^6$-DMSO) δ ppm (J Hz): 4.942 (t, 1H, J$_{1,2}$ 2.8 Hz, H$^1$), 4.428 (dd, 1H, J$_{2,1}$ 2.8 Hz, J$_{2,2'}$ 11.8 Hz, H$^2$), 4.319 (dd, 1H, J$_{2',1}$ 2.8 Hz, J$_{2',2}$ 11.8 Hz, H$^{2'}$)

compound (8)

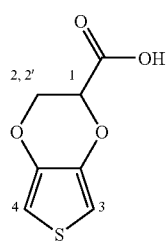

(300 MHz, d$^6$-DMSO) δ ppm (J Hz): 4.972 (t, 1H, J$_{1,2}$ 3.0 Hz, H$^1$), 4.367 (dd, 1H, J$_{2,1}$ 3.0 Hz, J$_{2,2'}$ 12.0 Hz, H$^2$), 4.220 (dd, 1H, J$_{2',1}$ 3.0 Hz, J$_{2',2}$ 12.0 Hz, H$^{2'}$), 6.581 (d, 1H, J$_{3,4}$ 3.6 Hz, H$^3$), 6.627 (d, 1H, J$_{4,3}$ 3.6 Hz, H$^4$)

Scheme 2. Synthesis of 2,3-dihydrothieno[3,4-b][1,4]dioxin-2,3-dicarboxylic acid, herein referred to as dicarboxylic acid EDOT monomer shown as Formula (II).

Formula (II)

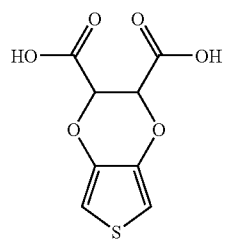

Scheme 2

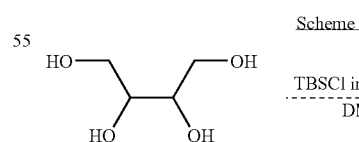

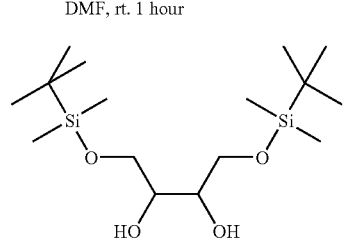

-continued

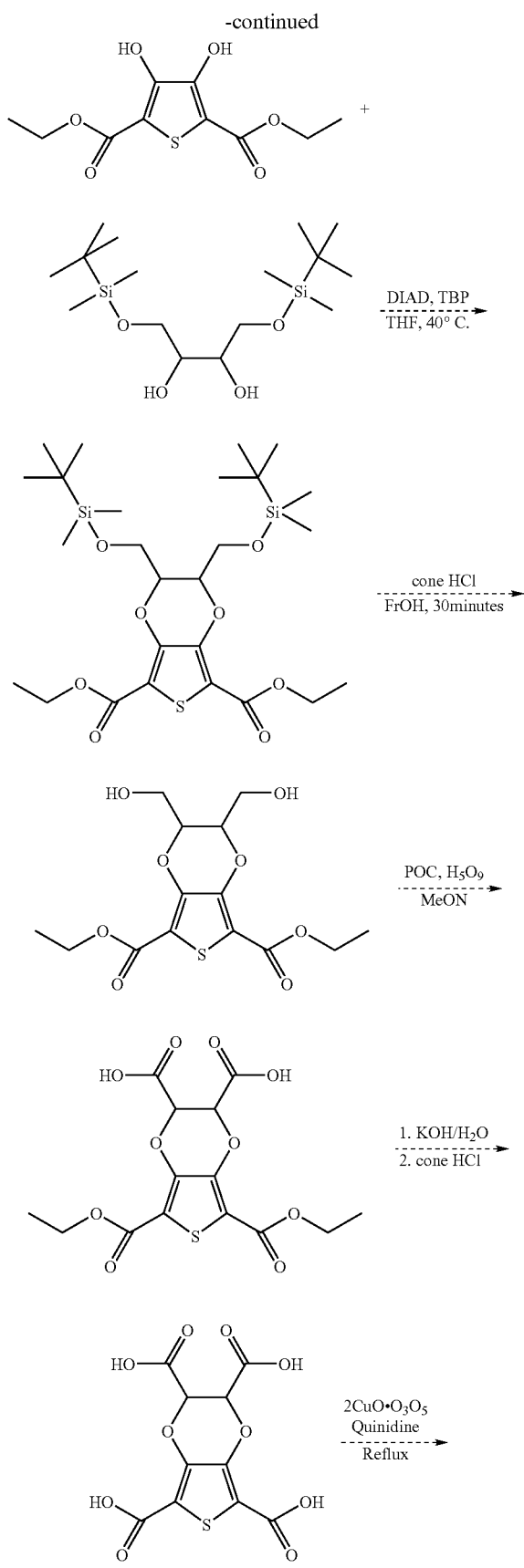

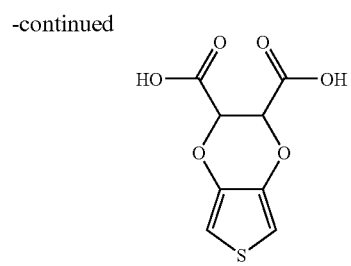

TBSCl = tert-butyldimethylsilyl chloride
DMAP = 4-dimethylaminopyridine
DMF = dimethylformamide
DIAD = diisopropylazodicarboxylate
TBP = tributylphosphine
THF = tetrahydrofuran In some embodiments, the diethyl 3,4-dihydroxythiophene-2,5-dicarboxylate (4) can be reacted with a protected form of butane-1,2,3,4-tetraol, DIAD and TBP and then oxidized to yield a second carboxylic acid group on the 1,4 dioxane portion of the molecule. In such cases, the 5,7-di(ethoxycarbonyl)-2,3-dihydrothieno[3,4-b][1,4]dioxin-2,3-dicarboxylic acid intermediate can also be treated with an aqueous solution of potassium hydroxide and then acidified with hydrochloric acid. After filtration, the product, 2,3-dihydrothieno[3,4-b][1,4]dioxin-2,3,5,7-tetracarboxylic acid can be decarboxylated by refluxing with copper chromite catalyst in freshly distilled quinoline to form the final product 2,3-dihydrothieno[3,4-b][1,4]dioxin-2,3-dicarboxylic acid. When the EDOT has been functionalized with two carboxylic acids, the dicarboxylic acid EDOT can be further functionalized with one or more functional groups, bifunctional groups, hetero-functional groups which can subsequently be conjugated with one or more bioactive molecules.

Synthesis of carboxylic acid EDOT according to Scheme 1 and dicarboxylic acid EDOT and PEDOT according to Scheme 2 have been developed to efficiently prepare carboxylic and dicarboxylic acid-modified EDOT (Formulas (I) and (II)) for bioconjugation and electrochemical polymerization. The carboxylic acid EDOT monomers synthesized in accordance to the present disclosure can be designed to have one or two carboxylic acid functional groups that can be used as universal coupling groups for bioconjugation with various biological molecules (e.g., peptides, proteins nucleic acids, carbohydrates, lipids and combinations thereof) using commonly known functional, bifunctional and hetero-functional coupling chemistries. Examples of preferred covalent attachment chemistries include amine, amide, ester, ether, and their heteroatom cognates, e.g., sulfonamide, thioether, and so forth. Typically, each pair of entities to be joined can jointly comprise a pair of reactive groups, such as a nucleophile and an electrophile, one respectively on each member of the pair.

Electropolymerization

As used herein, a carboxylic acid EDOT monomer can be polymerized into the carboxylic acid PEDOT polymer form. In some embodiments, the present bioconjugated films and coatings can comprise a mixture of carboxylic acid EDOT monomers mixed with varying amounts of EDOT to form copolymer carboxylic acid PEDOT. In some embodiments, the carboxylic acid PEDOT having one or more free COOH moieties for bioconjugation is a homopolymer of carboxylic acid EDOT. In some embodiments of the present disclosure, carboxylic acid EDOT (0.01 M) can be electropolymerized in $CH_2Cl_2$ with tetrabutylammonium perchlorate (TBAP, 0.05 M) on indium tin oxide (ITO) electrodes and silicon wafers sputtered with Au/Pd. Carboxylic acid EDOT and carboxylic acid EDOT/EDOT copolymer films can be made using a 1:1 mole ratio and 0.01 M total monomer. For comparison of electrical and chemical properties, films of EDOT with TBAP in $CH_2Cl_2$, can also be electropolymerized. In some embodiments, polymerizations can be galvanostatic with a current density between 0.1-0.5 mA/cm² and are performed for about 5 minutes to about 50 minutes, preferably from about 10 to about 20 minutes. The films can be washed with $CH_2Cl_2$ after polymerization and dried in air. After the carboxylic acid EDOT or carboxylic acid EDOT/EDOT film(s) or coating(s) can be applied to a substrate or electrode surface, the polymer films or coatings have stable electrochemical characteristics including reversible redox waves on cycling in either organic or aqueous buffers. In some embodiments, EDOT is first electrochemically polymerized with counter-ion (either PSS or lithium perchlorate) at current density of 0.1-0.5 mA/cm² for about 5 minutes to about 50 minutes. Carboxylic acid EDOT is then electrochemically polymerized with counter-ion (either PSS or lithium perchlorate) on top of the layer of PEDOT at current density of 0.1-0.5 mA/cm² for 10 minutes. 5 to 10 minutes at the current density of 0.1 mA/cm² may work to create a layer on top of the substrate or electrode surface, but 10 minutes can be used to ensure a film of carboxylic acid PEDOT has formed.

Coupling Bioactive Agents to Carboxylic Acid-PEDOT Films and Coatings

In some embodiments, the carboxylic acid EDOT can be directly electropolymerized onto electrically conductive solid or semi solid surfaces, for example, glass, metal, ceramic and carbon surfaces that are electrically conductive or contain electrically conductive elements in contact with the surface and subsequently conjugated to a bioactive molecule, for example a protein or peptide to form a biocompatible electrically conductive film or coating. In some embodiments, the carboxylic acid EDOT can be conjugated with the biomolecule first and then electrochemically polymerized onto a substrate or electrode in the form of a coating.

Carboxylic acid PEDOT polymer conjugated to an amino group containing biomolecule can be synthesized as shown in Scheme 3.

Scheme 3

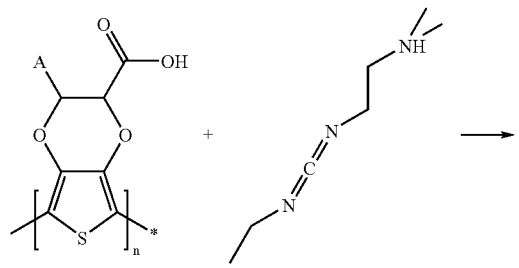

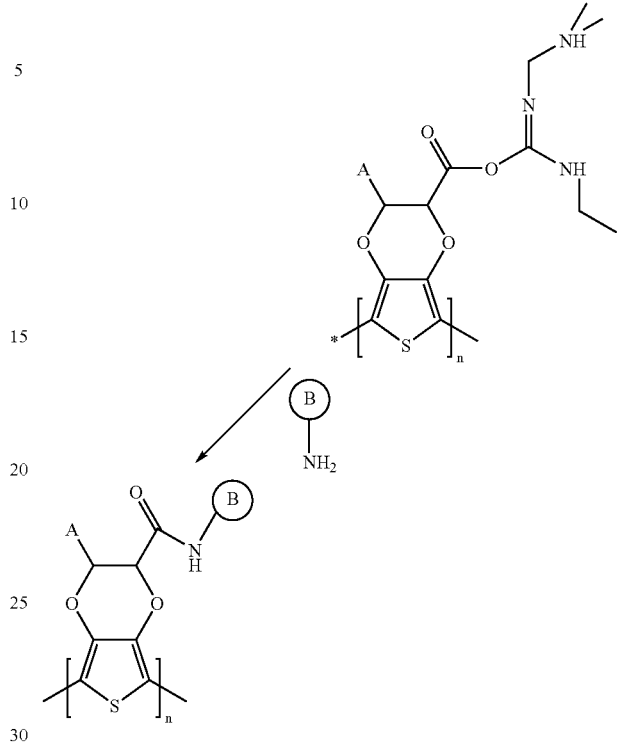

Carboxylic acid PEDOT can be coupled to a biomolecule to yield a biomolecule conjugated PEDOT Formula (III), for example, a peptide, by taking a sample of carboxylic acid PEDOT (from about 0.1 mg-to about 500 mg) and adding 50 microliters of 5 µM 1-[3-(Dimethylamino)propyl]-3-ethyl-carbodiimide methiodide in MES buffer (pH 6, MES=2-(N-morpholino)ethanesulfonic acid) per 0.3 cm² of film surface. The mixture can be left to sit while being agitated on a shaker plate for about 20 minutes. The activator is then removed, and the film can be rinsed twice with MES buffer. To this solution, 50 µL of 4 mg/ml GRGDS peptide in MES buffer can be added per 0.3 cm² of film surface. This is reacted for 24 hours while being agitated on a shaker plate. The samples can be rinsed with de-ionized water and then stored in PBS. The resultant coupled carboxylic acid PEDOT is shown in Formula (III).

Figure 1:
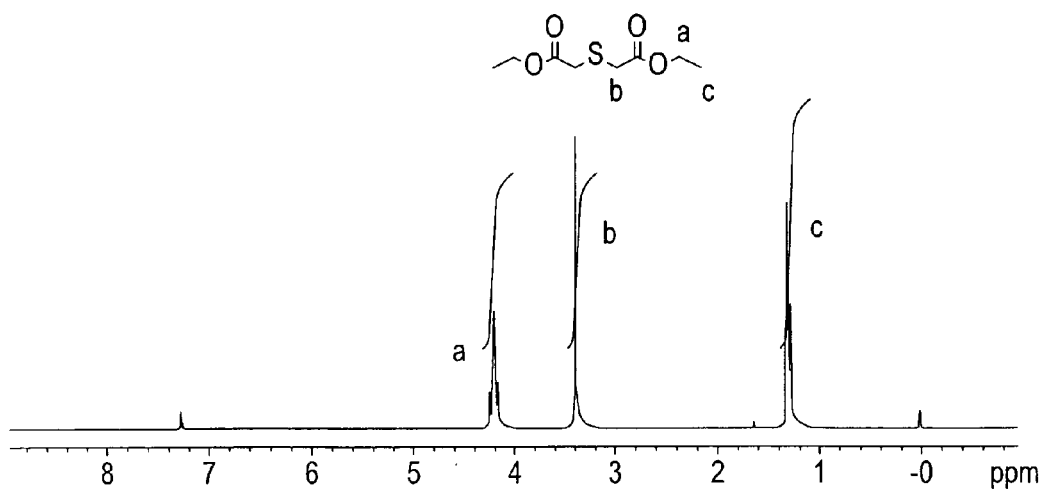
FIG. 1 depicts NMR spectra of intermediate (2) in $CDCl_3$ as synthesized in accordance with Scheme 1 of the present disclosure.
Figure 2:
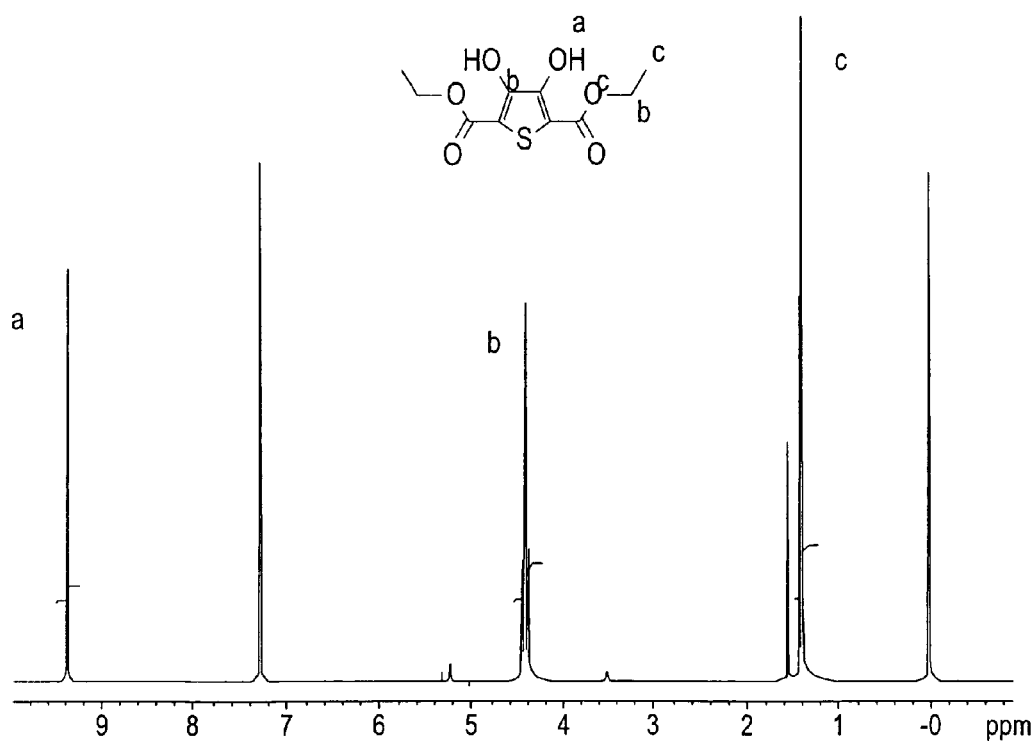
FIG. 2 depicts NMR spectra of intermediate (4) in $CDCl_3$ as synthesized in accordance with Scheme 1 of the present disclosure.
Figure 3:
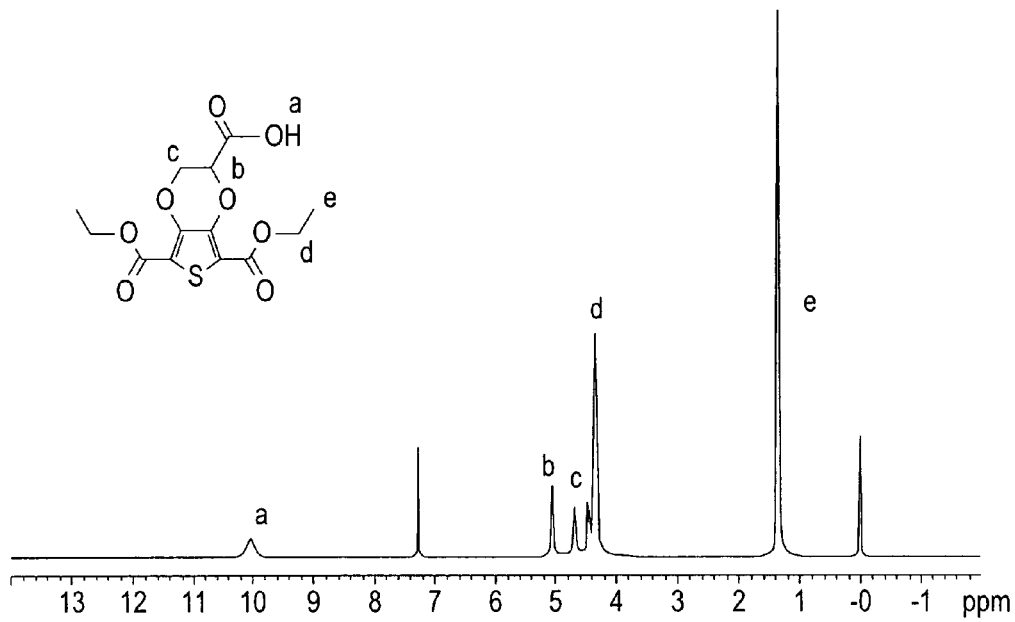
FIG. 3 depicts NMR spectra of intermediate (6) in $CDCl_3$ as synthesized in accordance with Scheme 1 of the present disclosure.
Figure 4:
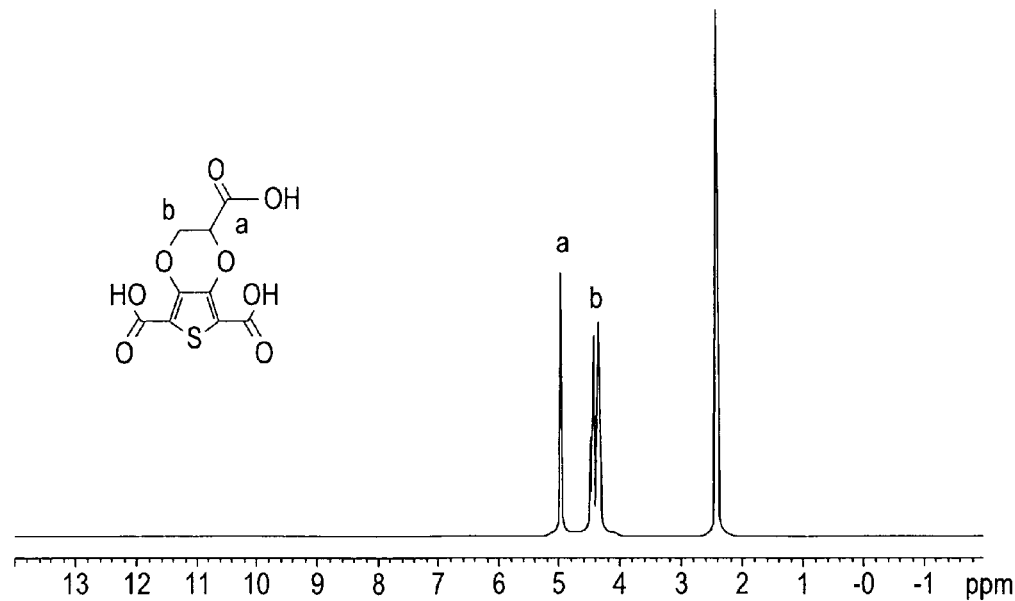
FIG. 4 depicts NMR spectra of intermediate (7) in $d^6$-DMSO as synthesized in accordance with Scheme 1 of the present disclosure.
Figure 5:
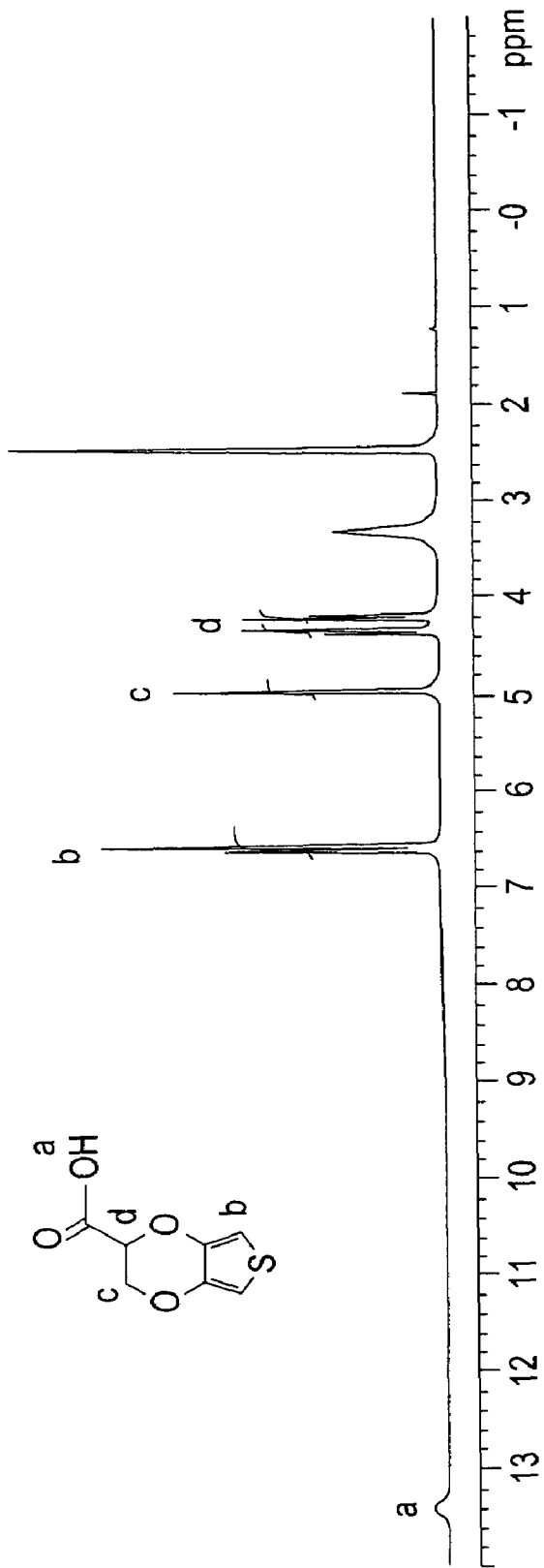
FIG. 5 depicts NMR spectra of intermediate (8) in $d^6$-DMSO as synthesized in accordance with Scheme 1 of the present disclosure.
Figure 6:
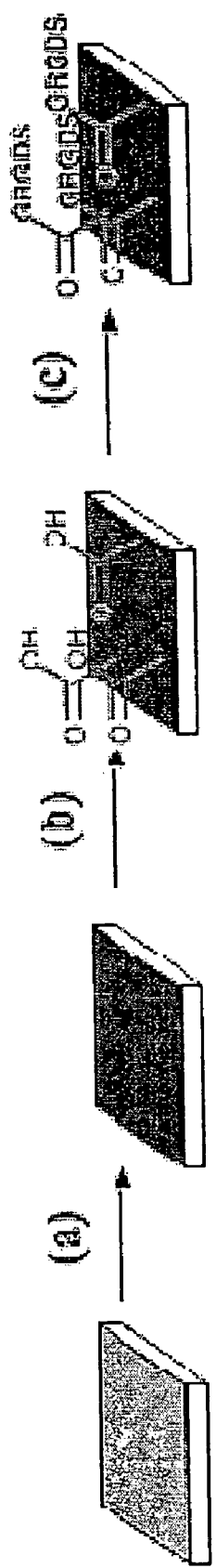
FIG. 6 depicts a reaction scheme involving carboxylic acid EDOT coupling using solid state coupling steps for the synthesis of bioconjugated electrically conductive polymer in accordance with the methods of the present disclosure.
Figure 7:
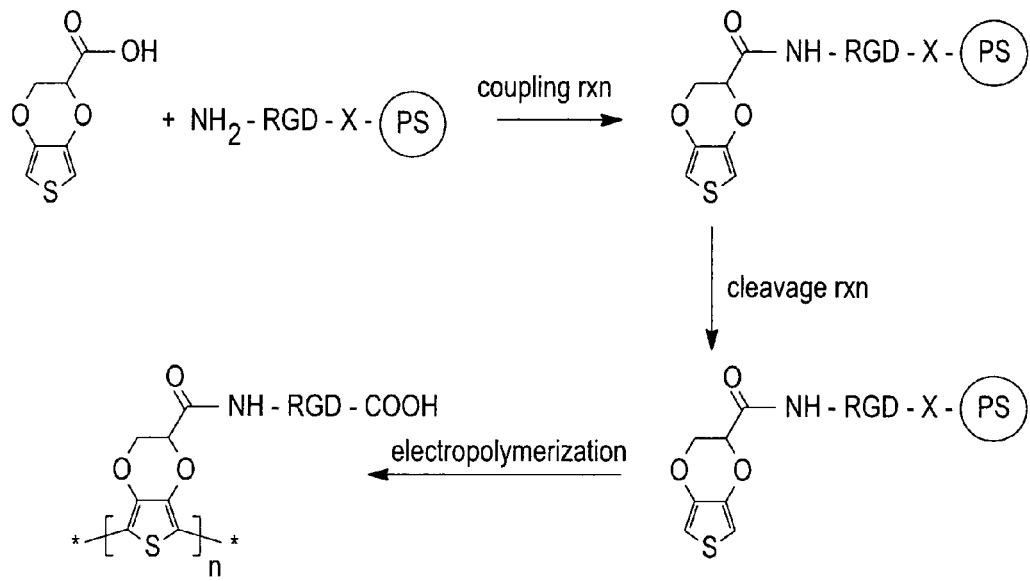
FIG. 7 depicts a reaction scheme involving coupling of carboxylic acid PEDOT using solution state coupling steps for the synthesis of bioconjugated electrically conductive polymer in accordance with the methods of the present disclosure.

In some embodiments, biocompatible conductive coatings and films comprising carboxylic and dicarboxylic acid EDOT compositions according to Formulas (I) and (II) can be made by electrochemically polymerizing the carboxylic and dicarboxylic acid EDOT monomer compositions in the presence of $LiClO_4$ counter ion on an electrically conductive substrate, for example a sputtered AuPd electrode. As shown in FIG. 6, films comprising polymerized EDOT and carboxylic acid EDOT can be made by first electrochemically depositing EDOT to form a first layer (a). Next, a second layer of carboxylic acid PEDOT is deposited or layered on the PEDOT layer by electropolymerizing carboxylic acid EDOT on the base PEDOT layer (b). In some embodiments, the number of layers of PEDOT and the number of layers of carboxylic acid-PEDOT can vary according to the type of application required. Next, the carboxylic acid functional groups on the PEDOT can be activated and then treated with a peptide in the presence of a coupling reagent, for example, a carbodiimide coupling reagent e.g. 1-Ethyl-3-[3-dimethylaminopropyl] carbodiimide hydrochloride or 1-(dimethylaminopropyl)-3- ethyl-carbodiimide hydrochloride for coupling amino or NH₂ groups to COOH functional groups on the EDOT or PEDOT as shown in FIGS. 7 & 8. Formula (III) shows the PEDOT polymer conjugated to a biomolecule designated B, only via one carboxylic acid group.

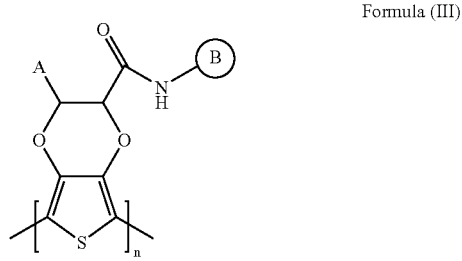

Formula (III)

In some embodiments, the A group of Formula I and III can comprise a second carboxylic group that can similarly be conjugated to a biomolecule via amide bond formation as in Scheme 3 or alternatively, a different coupling mechanism to yield a compatible covalent linkage between the biomolecule and the PEDOT A carboxylic acid functional group. In some embodiments, the B group of Formula (III) can be a peptide, a protein, for example an antibody, a receptor, a growth factor, for example, B can be a eukaryotic cell growth factor, e.g. a nerve growth factor, an insulin-like growth factor, s-myotrophin, a vascular smooth muscle cell growth factor, a vascular endothelial growth factor A and a beta-transforming growth factor, a lipid, a carbohydrate, for example, a saccharide or polysaccharide, a nucleic acid (e.g. deoxyribonucleic acids (DNA) consisting of small polynucleotide or oligonucleotide lengths of 7-50 nucleotides, nucleic acids of 50-10 kbp, ribonucleic acid (RNA), snRNA, siRNA, miRNA, nucleic acid mimetics, PNAs and combinations thereof.

Methods of coupling carboxylic acid groups to various biologically active side groups including amino groups and phosphate groups have been described in various coupling methodologies using coupling reagents commercially available through Pierce Inc. (Rockford, Ill. USA).

In some embodiments, methods are provided to synthesize and characterize RGD-functionalized PEDOT. To achieve this goal, carboxylic acid functionalized EDOT can be synthesized to allow conjugation between carboxylic acid EDOT and the peptide using various coupling chemistries, including for example carbodiimide based coupling shown in FIGS. 7 and 8. The resulting amide linkage will be uniquely stable during the deprotection step of amino acids used. Other commercially available or reported functionalized EDOT can produce a linker with peptides that is unstable through the deprotection step. In some embodiments of the present disclosure, methods are provided for a synthetic route to make carboxylic acid-functionalized EDOT (carboxylic acid EDOT) as shown in Scheme 1. Carboxylic acid EDOT monomer can be successfully synthesized, characterized, and electropolymerized to form carboxylic acid PEDOT polymer. In some embodiments, a polymer film along with a copolymer film of carboxylic acid PEDOT and PEDOT have been partially characterized. In some embodiments, conjugation of the peptide RGD to both carboxylic acid EDOT and carboxylic acid PEDOT can be performed as described in the coupling schemes shown in FIGS. 7 and 8 respectively. Subsequent characterization of the films can be made with X-ray photoelectron spectroscopy, cyclic voltammetry, impedance spectroscopy, and in vitro cell experiments. While other PEDOT derivatives have been presented in literature (such as those with sulphonate groups, biotinylated side-chains, and oligonucleotide side-chains), the present disclosure provides for novel biomolecule-conjugated PEDOT compositions and methods of preparing such compositions.

In certain embodiments of the present disclosure, the conductive polymers are functionalized with carboxylic acid and conjugated to biomolecules with compatible coupling groups to COOH for example amino, phosphate, thiol, sulfhydryl, thiocyanate and disulfide groups. For example, RGD or GRGDS amino acid containing peptides can be coupled to the carboxylic acid EDOT monomers and carboxylic acid PEDOT polymers using reaction Scheme 3.

In some embodiments, the conducting polymers can include, but are not limited to: poly(3,4-ethylenedioxythiophene) (PEDOT), polythiophenes, polymer blends thereof, and composites with the ability to conduct electronic charge or ions, and hybrid polymer-metal materials that are electrically or ionically conductive. Other conductive polymers can include functionalized copolymers that are made from EDOT and other conducting polymers that are functionalized with carboxylic acid and conjugated to biomolecules, including peptides and proteins for example, RGD, IKVAV, YIGSR, KDEL peptides and combinations thereof, for example RGD and YIGSR, and other biomolecules containing chemically compatible functional groups that can be covalently attached using standard coupling chemistries to the functionalized conducting monomer, for example carboxylic acid-EDOT. A covalent attachment can be effected using any covalent chemistry described herein. Typically, each pair of entities to be joined can jointly comprise a pair of reactive groups (such as a nucleophile and an electrophile), one respectively on each member of the pair, as shown in the coupling reactions in FIGS. 7 and 8. Where the biological entity (tissue, cell, cell fragment, organelle, or other biologic) is to be directly attached to the monomer or polymer, each will contain one reactive group of a pair. In some embodiments, the biomolecule can be covalently attached to a linker. Where attachment is to take place through a linker, the linker can contain two reactive groups, one of which is capable of covalently reacting with a reactive group of the carboxylic acid EDOT monomer and the other of which is capable of covalently reacting with a reactive group of the biological entity. The reactive group(s), such as carboxylic acid, can be already present as part of the monomer (e.g., carboxylic acid EDOT). Where attachment is to take place through a linker, the linker can be attached first to the polymer, first to the biological entity, or concurrently to both. Non-limiting examples of preferred nucleophile and electrophile groups for use in forming a covalent attachment are presented in Table 1.

TABLE 1

Exemplary Reactive Group Pairs For Attachment Chemistries between the biomolecule and the functional group on the EDOT monomer or PEDOT polymer

| Nucleophile | Electrophile | Attachment |
|---|---|---|
| Amine | Alkyl carbodiimide-activated ester | Amide |
| | Bromoacetamide | Amine |
| | Carboxyl | Amide |
| | Chloroacetamide | Amine |
| | Cyclic carboxylic anhydride | Amide |
| | 9-Fluorenylmethoxycarbonyl | Amide |
| | N-Hydroxysuccinimide ester | Amide |
| | Isocyanate | Urea |
| | Isothiocyanate | Thiourea |

TABLE 1-continued

Exemplary Reactive Group Pairs For Attachment Chemistries between the biomolecule and the functional group on the EDOT monomer or PEDOT polymer

| Nucleophile | Electrophile | Attachment |
|---|---|---|
| | Phosphate | Phosphoramide |
| | Phosphonate | Phosphonamide |

In some embodiments, conducting polymers can be any non-conductive monomer or polymer that can be made conductive in the presence of an appropriate doping system. In some embodiments, conjugated polymers described herein are functionalized by chemically synthesizing the electrically conductive monomer or polymer to contain functional side groups (e.g., carboxylic acid) that can allow for binding of peptides, proteins, lipids, carbohydrates and nucleic acids before or after polymerization. In some embodiments, the conductive polymer can be biodegradable and will dissolve in the presence of biological fluid, for example, when the device is implanted in situ (e.g., implantable brain prostheses, neural stimulators, transient heart devices, and the like. The biodegradable conducting polymer can include, for example, polypyrrole and poly(3,4-ethylenedioxythiophene) block PEG, and poly(3,4-ethylenedioxythiophene) PEDOT, tetramethacrylate and others that are commercially available from TDA Research Inc., Wheat Ridge, Colo., USA.

Conductive carboxylic acid monomers for example EDOT, contemplated by the present disclosure typically require counter ions for polymerization and electroconductivity across the electrode-tissue interface. The conducting polymers are reacted with a polyelectrolyte at the molecular level. Electron delocalization is a consequence of the presence of conjugated double bonds in the conducting polymer backbone. To make the conducting polymers electrically conductive, it is necessary to introduce mobile carriers into the double bonds, which is achieved by oxidation or reduction reactions (called "doping"). The concept of doping distinguishes conducting polymers from all other kinds of polymers. This process can be assigned as p-doping or n-doping in relation to the positive or negative sign of the injected charge in the polymer chain by analogy to doping in inorganic semiconductors. These charges remain delocalized, being neutralized by the incorporation of counter-ions (anions or cations) denominated dopants. Suitable dopants and methods of doping are known to those skilled in the art, e.g. from EP 0 528,662 and U.S. Pat. No. 5,198,153 or WO 96/21659. In certain embodiments, ionic electrolytes or dopants used to polymerize conducting polymers include, but are not limited to: poly(styrene sulfonate) (PSS; Sigma Aldrich, St. Louis, Mo., USA), $LiClO_4$, Phosphate-buffered saline (PBS; HyClone, Logan, Utah, USA), Hank's Balanced Salt Solution (HBSS, HyClone), Collagen, Poly-D-Lysine (PDL), Poly-L-Lysine, poly-ornithine, and bioactive molecules of interest having the appropriate ionic charge for the type of doping system used and can include, but is not limited to: dexamethasone or other anti-inflammatory agents, antibiotics, anti-mitotics, growth factors, scar-reducing drugs, poly acrylic acid, dodecylbenzene sulfonic acid (DBSA), p-toluenesulfonic acid (p-TSA) and combinations thereof. When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6-H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO^{3-}$, $ClO_4^{3-}$, $BF_4^-$, $PF_6^-$, $AsF_6^-$, $SbF_6^-$, $FeCl_4^-$, $Fe(CN)_6^{3-}$), and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O^2$, $XeOF_4$, $(NO_2^+)$ $(SbF_6^-)$, $(NO_2^+)$ $(SbCl_6^-)$, $AgClO_4$, $H_2$ $IrCl_6$, $La(NO_3)_3 6H_2O$, $FSO_2OOSO_2F$, Eu, acetylcholine, $R_4N+$, (R is an alkyl group), $R_4P^+$ (R is an alkyl group), $R_6As^+$ (R is an alkyl group), and $R_3S^+$ (R is an alkyl group).

Characterization

The electrodes, electrode-based devices, films and coatings used to modify preexisting electrodes can optionally include controllers, analyzers and other sensing devices and computers that can be used to control the output of electrical current, or voltage. These optional components can also be used to perform, measure and record electrical events, current flow, electrical impedance spectroscopy, cyclic voltammetry, resistance, conductance, capacitance, and potential of the integrated network to the flow of electrons. These analytical systems and devices are commercially available (e.g., the Brinkman's (Eco Chemie) Autolab system connected to various CPU's (Windows or Macintosh computers) available from Brinkman Instruments Inc., Westbury, N.Y., USA).

The appearance of the carboxylic acid PEDOT, PEDOT-acid/PEDOT copolymer, PEDOT films and carboxylic acid-biomolecule conjugated PEDOT can be characterized using optical microscopy. The chemical compositions can be investigated using X-ray photoelectron spectroscopy (XPS). Cyclic voltammetry (CV) from 0.5 to −0.9 V along with electrochemical impedance spectroscopy (EIS) can be used to characterize the electrical properties of the films.

In some embodiments, the PEDOT-acid, PEDOT-acid/PEDOT copolymer, and PEDOT films can form bluish-green films on both ITO and Au/Pd electrodes. The polymer formed a well-adhered film on the Au/Pd electrode, but can delaminate off the ITO electrodes after polymerization. As shown in FIGS. 9 and 10, the XPS characterization was performed using the Kratos Axis Ultra XPS in EMAL (http://www.e-mal.engin.umich.edu/instruments/xps.html) with the monochromatic Al x-ray source. The spectra were all shifted so that the C—C peak is at 285 eV.

FIG. 9 illustrates a graph showing the C 1s XPS spectra for the PEDOT, carboxylic acid-PEDOT film on top of a layer of PEDOT, PEDOT treated with GRGDS peptide and the carboxylic acid PEDOT-GRGDS peptide copolymer film. The C 1s XPS spectrum in FIG. 9 supports that the carboxylic acid functionalized EDOT has polymerized on the top of the PEDOT film.

FIG. 10 depicts N 1s XPS spectra demonstrating that the peptide coupling process appears to be successful. There are 2 peaks for the peptide-treated sample, which are from the amide peptide backbone and from the side chain in the amino acid arginine (R). The control samples do have a nitrogen peak and we are currently investigating the source of this nitrogen. It is predicted that the contamination is due to impurities introduced during the electrochemical polymerization process.

As shown in FIG. 11, the Electrochemical Impedance Spectroscopy (EIS) spectra for a PEDOT homopolymer film, a carboxylic acid PEDOT film on top of a layer of PEDOT (both with PSS dopant) and a bare Au/Pd electrode are compared. The electrodes used to measure the impedance of the two films prepared in accordance with FIG. 6 and bare electrode were 6 mm barbell AuPd electrodes. The measurements were taken using an Autolab potentiost/galvanostat using a 3-electrode cell (working, counter and Ag/AgCl reference electrode). The electrodes were immersed in a PBS/water electrolyte. Impedance measurements were taken using Frequency Response Analyze version 4.9.005 software and the cyclic voltammetry (CV) measurements were taken using General Purpose Electrochemical System version 4.9.005 software. Both the impedances of the carboxylic acid PEDOT and PEDOT have similar electrical properties. Both films decrease the impedance of the electrode at all frequencies, which is an important property for biological interface applications.

FIG. 12 shows the CV curves as an average of 5 cycles. The CV curves shown in FIG. 12 demonstrate slightly different behavior between the carboxylic acid PEDOT on top of a layer of PEDOT and PEDOT coatings, since the carboxylic acid PEDOT film prepared in accordance to FIG. 6 has a higher charge capacity. Both polymer films demonstrate some charge capacity, especially compared to the bare Au/Pd electrode.

In some embodiments, both solid-state and solution coupling methods can be used and are shown in FIGS. 7 and 8 respectively, for films in which the carboxylic acid EDOT is conjugated to the peptide before electropolymerization and for films produced where the carboxylic acid EDOT is electropolymerized into carboxylic acid PEDOT first, then the carboxylic acid moieties in the polymer are coupled with RGD peptides. For solution-state coupling, one end of the peptide can be attached to a polystyrene bead with a weak covalent linkage. The carboxylic acid EDOT can be coupled with the free end of the peptide to form an amide bond and after coupling, the link between the polystyrene bead and the peptide will be cleaved to yield a free carboxylic acid. Electropolymerization can be performed after the coupling reaction to form RGD-functionalized PEDOT. For solid-state coupling, electropolymerization can be performed first in order to form a carboxylic acid PEDOT homopolymer film on the substrate, or on a substrate first coated with PEDOT or other conjugated electroconductive polymer as shown in FIG. 6 with PEDOT. Before coupling, the peptide can be cleaved from the polystyrene bead and, in order to prevent unwanted reactions, a protecting group can be added to the carboxylic acid end of the peptide. After the protecting group is added, the peptide can be coupled with carboxylic acid PEDOT to form a biomolecule conjugated electrically conductive polymer. The protecting group will then be removed; resulting in the formation of RGD-conjugated PEDOT film or coating. In some cases protecting groups on the peptide are not necessary and the peptide can be coupled without interference from functional groups. This allows the peptide coupling to be performed in water and also eliminates damage caused to the polymer film by the harsh deprotection reaction conditions.

In some embodiments, RGD-conjugated PEDOT can be characterized using XPS, EIS, CV, and, most importantly, cell experiments. In some embodiments, the RGD-conjugated carboxylic acid EDOT is water-soluble and can be polymerized around living cells, to form biologically integrated bioelectrode devices comprising a first electrically conductive substrate, a biological component (such as a tissue cell, cell membrane or synthetic cell or micelle), and a conductive polymer film or coating conjugated with a biomolecule. The conductive polymer (i.e. a film or coating on an electrode consisting of a biomolecule coupled to PEDOT) couples the conductive substrate (e.g., an electrode) to the cells or tissue to collectively define a bioelectrode. In some embodiments, the bioelectrode is capable to transmit or receive an electrical signal between the electrode and either or both of the cells or tissues and conductive polymer.

Applications for Bioconjugated Electroconductive Films

In some embodiments, films and coatings comprising the carboxylic acid functionalized EDOT monomer as shown in Formula I can serve as an enhanced substrate for binding of other electroconductive polymers. In some embodiments, the acid-EDOT of the present disclosure can be electropolymerized onto a variety of surfaces including metallic surfaces including, for example, gold, silver, platinum, iridium, indium tin oxide, titanium and tungsten. In some embodiments, other functional groups can be attached to the free carboxylic acid moiety on the conjugated PEDOT films and coatings which enable the functionalized conjugated PEDOT films to bind to difficult to bind metal surfaces such as stainless steel. In this sense, the acid-PEDOT films and coatings of the present disclosure can act as adhesion promoters for other materials, including PEDOT and other electroconductive conjugated polymers. As illustrative examples, functionalized PEDOT films of the present disclosure can then serve as a substrate for subsequent binding of other conjugated electconductive polymers including PEDOT, polypyrrole, polyaniline, polyacetylenes, polythiophenes and blends thereof.

Limitations associated with electropolymerization of conducting polymers in biological tissues can include problems with the focal adhesion of neural cells after polymerizing EDOT directly around living cells. PEDOT when polymerized around cells can grow on top of the extracellular matrix (ECM), thus preventing the cells from creating focal contacts with the ECM proteins. The lack of adhesion can be demonstrated by the loss of actin stress fibers in the cells and eventually cell death occurs. Since the peptide sequence RGD is known to promote cell adhesion to the ECM, the functionalization of electrically conductive PEDOT polymer with RGD should promote the formation of focal contacts between neural cells and the PEDOT film. Therefore, after polymerization of the PEDOT around living cells, the actin stress fibers should remain intact, which will make long-term cell survival more probable.

EXAMPLES

Example 1

Biologically Compatible Probes

An electrochemical cell probe was produced to determine whether a biomolecule functionalized PEDOT film could be used to enhance the compatibility between the electrode and the mouse skeletal muscle cell line C2C12 cells. The biomolecule functionalized PEDOT film was produced in accordance to the PEDOT/carboxylic acid PEDOT layered film described in FIG. 6. The substrate was coated with a layer of PEDOT followed by a plurality of layers of carboxylic acid PEDOT doped with poly(styrenesulfonate)(PSS) in accordance with the present disclosure. To the carboxylic acid PEDOT present on the substrate, RGD was coupled to the available COOH groups on the carboxylic acid PEDOT using 1-(dimethylaminopropyl)-3-ethyl-carbodiimide hydrochloride. The resultant conjugated RGD-PEDOT/PSS substrate was subsequently rinsed in physiological buffer and prepared for cell culture of C2C12 cells. C2C12 cells were seeded at a density of $1 \times 10^5$ cells per well in 6 well cell culture plates without serum. The conjugated PEDOT/PSS was compared to conjugated RGD-PEDOT/PSS by adding the mouse skeletal muscle cell line C2C12 onto the two substrates to determine which substrate provided a more biocompatible surface for attachment and growth of the C2C12 cells in vitro. Cells were seeded for 4 hours before fixing with formaldehyde and then staining with phalloidin.

As shown in FIGS. 13A and 13B, F-actin staining of C2C12 cells on PEDOT-PSS (FIG. 13A) and PEDOT-PSS-RGD (FIG. 13B) reveals that most C2C12 cells on PEDOT-PSS have a very round morphology whereas the cells on PEDOT-PSS-RGD have long extensions, indicating attachment. These results suggest that electrically active cells, for example, C2C12 cells are more likely to attach and grow on PEDOT-PSS-RGD containing substrates and coatings than PEDOT alone. The enhanced compatibility of biomolecule conjugated PEDOT according to the present disclosure can be individually manipulated for a particular cell or tissue type by matching a peptide, growth factor, cytokine, cluster of differentiation marker (CD) marker that can attract the cell type or induce growth and extension of the cell on the biomolecule conjugated PEDOT substrate.

In some embodiments, the activity, growth and differentiation of various electrically active cells including skeletal muscle cells, cardiac muscle cells for example cardiomyocytes and brain tissue cells, for example neurons can be sensed by growth of these cells on the films and coatings comprising the biomolecule conjugated PEDOT films and coatings of the present disclosure.

Neural probes capable of electrical sensing and recording using PEDOT are superior to bare electrodes when implanted into the brain. These PEDOT probes however, have some limitations, including growth of the PEDOT on top of the extracellular matrix (ECM), thus preventing the cells from creating focal contacts with the ECM proteins. The lack of adhesion is demonstrated by the loss of actin stress fibers in the cells and eventually cell death occurs. In some embodiments, a neurological sensing probe or probe array commonly used for recording electrical activity in various portions of the brain can be conjugated with a biomolecule for example an RGD peptide or growth factor for example nerve growth factor in accordance with the functionalizing and conjugation methods of the present disclosure, to render the electrode or array more biologically compatible with the neural cells in contact with the probe or array of probes.

In some embodiments, the present biomolecule conjugated conductive substrates comprising biomolecule conjugated PEDOT (Formula III) can be used to identify and screen for biomolecules such as organic molecules, peptides, proteins, carbohydrates and lipid molecules capable of enhancing growth or inhibiting cell death when incubated with an electrically active cell. As an illustrative example, collateral sprouting of axons from the peripheral nervous system (PNS) into the central nervous system (CNS) appears to involve the action of a growth factor with properties similar to NGF. The identification of specific molecules such as those found in small molecule libraries, combinatorial libraries or peptide libraries (Commercially available from GenScript, Piscataway, N.J. USA). The peptides or other small molecules can be functionalized by adding a compatible functional group, for example an $NH_2$ or amino group that can be conjugated to COOH functional group on the PEDOT. Other coupling strategies commonly known can be employed in establishing a direct coupling between the COOH group of the PEDOT polymer and the corresponding functional group on the candidate molecule. The library can be disposed on a substrate for example a metallic, silicon or glass slide in single or an array pattern. The substrate is preferably electrically conductive and can accommodate the electropolymerization of carboxylic acid EDOT to carboxylic acid PEDOT on the substrate. The COOH groups of the carboxylic acid PEDOT can then be conjugated with a compatible functional group on the peptide or small molecule in the library. The degree of attachment, growth or differentiation of electrically active cells, for example, neurons to the individual spots on the array can be electrically determined by measuring the shift in redox potential and/or capacitive charging element in the cyclic voltammogram (as shown in FIG. 13 herein). Alternatively, the substrate containing the peptide library or small molecule library incubated with cells can be stained with an antibody that is capable of measuring a cell skeletal protein, such as actin, to indicate differentiation and growth of the cells. Identification of candidate molecules that are capable of affecting neuronal growth should lead to an understanding of the etiology of degenerative neurological diseases such as Alzheimer's disease and, hopefully, to rational therapeutic approaches.

Example 2

Biomolecule Sensing Chip

In some embodiments, the present disclosure provides for films and coatings that are capable of sensing specific binding events between two biomolecules, for example, an enzyme and its cognate ligand, or a single strand of a polynucleotide and its complementary binding polynucleotide. In some embodiments, an electrically conductive substrate is provided that has been electropolymerized with a layer of PEDOT or carboxylic acid PEDOT. To the first layer, a second layer or region (which can include one or more spots or an array of spots) of conjugated electroconductive polymer such as carboxylic acid PEDOT, PEDOT, polyaniline, polypyrrole, polythiophene or combinations thereof is electropolymerized. The second layer or region can be functionalized with carboxylic acid or carboxylic acid and any further functional groups commonly known to react with COOH to form a new and different functional group in accordance with the present disclosure or methods of functionalizing COOH groups known in the art. To the substrate a biomolecule functionalized with a compatible functional group capable of attaching covalently to either a COOH group or a different functional group, for example amine, amide, hydroxyl, thiol, haloacyl or haloacetyl and SH. The nucleophilic group of the modifying compound is selected from amine group, a hydroxyl group, a thiol group, hydrazide and a guanidino group.

In some embodiments, the biomolecule can be attached to a bifunctional linker selected from the group of bifunctional linkers having a nucleophilic group or a combination of such bifunctional linkers. In some embodiments, the functional group can be any nucleophilic group from an amine group, a hydroxyl group, a thiol group, a guanidine group and hydrazide. Suitable bifunctional linkers are well known in the art and can be found, for example, in the catalog of the Pierce Company, Rockford, Ill. USA (Pierce 2005-2006 Applications Handbook & Catalog at www.piercenet.com).

In some embodiments, the biomolecule can be any one or more of a peptide, protein or a polynucleotide and combinations thereof. The biomolecule can be treated to ensure that free primary amino groups are available for conjugation with the substrate layered carboxyl acid PEDOT. Naturally, proteins have one or more primary amino groups. Oligonucleotides can also be conjugated to primary amine-containing molecules by modifying the 5' phosphate group of oligonucleotides using the carbodiimide crosslinker EDC and imidazole and amine-modification of the oligonucleotide with an excess of ethylenediamine as described in TECH TIP #30 "Modify and label oligonucleotide 5' phosphate groups." Pierce Company, Rockford Ill. USA. The anchoring of the biomolecule onto the conductive substrate can be verified by reflectance infrared spectroscopy or changes in electrochemistry of the conjugated COOH-PEDOT.

The carboxylic acid PEDOT film and substrate coatings of the present disclosure can be coupled to a variety of biomolecules described above for the detection and quantification of target ligands and complementary polynucleotides for the detection of DNA or RNA in a test sample. With reference to DNA and RNA molecules the nucleic acids can first be functionalized to add a primary amino group first to generate for example, oligonucleotides can be incubated with a carbodiimide crosslinker e.g. EDC (Pierce Co., Rockford, Ill. USA). The oligonucleotide as an ester intermediate is then incubated with imidazole to yield a reactive phosphorylimidazolide. The phosphorylimidazolide is then incubated with excess ethylenediamine to produce a phosphoramidate oligonucleotide that can be conjugated to a carboxylic or dicarboxylic acid EDOT of Formula I or II or alternatively to carboxylic acid PEDOT (Formula III). In some embodiments, the oligonucleotide can be synthesized using automated oligonucleotide synthesis as phosphoramidate oligonucleotides commercially available from Operon Biotechnologies Inc., Huntsville, Ala. USA. The conjugated PEDOT-oligonucleotides can be deposited onto an electrically conductive substrate, for example, silica, metal or glass substrates with electrically conductive elements and reacted with a test nucleic sample or multiple nucleic acid samples. The deposition process can involve any commonly known patterning deposition technique, for example, ink jet printing, multi-pipette deposition and the like. Upon binding of the conjugated biomolecule to its cognate ligand or complementary DNA or RNA sequence, a change in the electrochemical properties of the film and coatings can be detected using electrical impedance spectroscopy XPS binding plots and cyclic voltammetry thus illustrating their applicability as films and coatings for Protein/peptide and DNA/RNA chips.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An electroconductive carboxylic acid functionalized monomer corresponding to Formula (I),

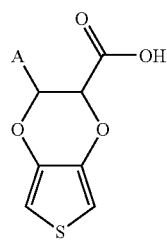

wherein A represents a hydrogen or a carboxyl group.

2. The electroconductive carboxylic acid functionalized monomer according to claim 1, wherein A represents a hydrogen.

3. The electroconductive carboxylic acid functionalized monomer according to claim 1, wherein A represents a carboxyl group.

4. The electroconductive carboxylic acid functionalized monomer according to claim 1, further comprising a conjugated biomolecule, wherein said carboxylic acid group of said monomer is coupled to an amino group on said biomolecule with a carbodiimide containing compound to form an amide bond with said biomolecule.

5. An electroconductive film or substrate coating with charge transport properties comprising a polymer and a dopant, said polymer comprising polymerized carboxylic acid functionalized monomer corresponding to Formula (I):

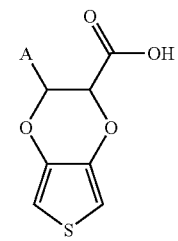

wherein A represents a hydrogen or carboxyl group.

6. An electroconductive film or substrate coating according to claim 5, wherein said polymer is conjugated to one or more of a peptide, a protein, a lipid, a carbohydrate or a polynucleotide.

7. The electroconductive film or substrate coating of claim 5, further comprising a polymer selected from the group consisting of poly 3,4-ethylenedioxythiophene (PEDOT), polypyrrole, polyanilines, polyacetylenes, polythiophenes, and blends thereof.

8. The electroconductive film or substrate coating of claim 5 wherein the dopant is selected from the group consisting of poly(styrenesulfonate), phosphate-buffered saline, Hank's Balanced Salt Solution, collagen, poly-D-Lysine, poly-L-Lysine, poly-ornithine, dexamethasone, antibiotics, anti-mitotics, growth factors, scar-reducing drugs, poly acrylic acid, dodecylbenzene sulfonic acid, p-toluenesulfonic acid and combinations thereof.

9. The electroconductive film or substrate coating of claim 5, further comprising an electrically conductive substrate wherein said film or substrate coating is disposed on a surface of said conductive substrate.

10. The electroconductive film or substrate coating of claim 9, wherein said film or substrate coating is polymerized on a layer of PEDOT, said layer of PEDOT being polymerized on a surface of said electrically conductive substrate.

11. A biomolecule conjugated PEDOT polymer comprising a monomer of the formula:

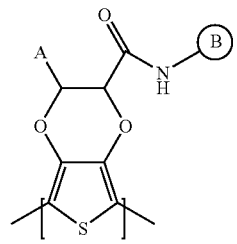

wherein A is a hydrogen or a carboxylic acid group; and B is a first biomolecule selected from the group consisting of a peptide, a protein, a lipid, a carbohydrate and a polynucleotide.

12. The biomolecule conjugated PEDOT polymer according to claim 11, wherein A is a hydrogen.

13. The biomolecule conjugated PEDOT polymer according to claim 11, wherein A is a carboxylic acid group.

14. The biomolecule conjugated PEDOT polymer according to claim 11, wherein B is a peptide selected from the group consisting of RGD, GRGDS, IKVAV, CDPGYIGSR, YIGSR, KDEL and combinations thereof.

15. The biomolecule conjugated PEDOT polymer according to claim 11, wherein B is a eukaryotic cell growth factor comprising a nerve growth factor, an insulin-like growth factor, s-myotrophin, a vascular smooth muscle cell growth factor, a vascular endothelial growth factor A and a beta-transforming growth factor.

16. The biomolecule conjugated PEDOT polymer according to claim 11, wherein B is a phosphoramidate polynucleotide having 7 to 50 nucleotides.

17. The biomolecule conjugated PEDOT polymer according to claim 11, wherein when A is a carboxylic acid group, A is coupled to a second biomolecule via an amide bond, and said first and second biomolecules can be the same or different.

18. The biomolecule conjugated PEDOT polymer according to claim 11, which is oxidatively or reductively doped to form a conducting ionic polymer.

19. An electrically conductive substrate having a first layer of PEDOT polymerized on a surface of said substrate and a second layer of biomolecule conjugated PEDOT polymer of claim 11 polymerized on said first layer of PEDOT, said first and second layers forming a charge transport material in electrical communication with said conductive substrate.

20. The electrically conductive substrate of claim 19, further comprising a dopant.

\* \* \* \* \*

UNITED STATES PATENT AND TRADEMARK OFFICE
CERTIFICATE OF CORRECTION

PATENT NO. : 7,708,908 B2
APPLICATION NO. : 12/038138
DATED : May 4, 2010
INVENTOR(S) : Jinsang Kim et al.

It is certified that error appears in the above-identified patent and that said Letters Patent is hereby corrected as shown below:

Col. 4, line 30, "Formula I" should be --Formula (I)--.

Col. 7, line 3, "[3,4-b]dioxin-5,7 dicarboxylate" should be --[3,4-b] [1,4] dioxin-5,7-dicarboxylate--.

Col. 7, line 67, "2.0 Hz" should be --12.0 Hz--.

Col. 13, line 19, "Formula I and III" should be --Formula (I) and (III)--.

Col. 17, line 4, "potentiost/galvanostat" should be --potentiostat/galvanostat--.

Col. 18, line 8, "Formula I" should be --Formula (I)--.

Col. 19, line 48, "(Formula III)" should be --(Formula (III))--.

Col. 21. line 22, "Formula I or II" should be --Formula (I) or (II)--.

Col. 21, line 23, "(Formula III)" should be --(Formula (III))--.

Signed and Sealed this

Twenty-third Day of November, 2010

David J. Kappos
*Director of the United States Patent and Trademark Office*